US007927805B2

(12) United States Patent
Raponi et al.

(10) Patent No.: US 7,927,805 B2
(45) Date of Patent: Apr. 19, 2011

(54) PROCESS FOR PREDICTING THE PROGNOSIS OF SQUAMOUS CELL LUNG CANCER

(75) Inventors: Mitch Raponi, Media, PA (US); Lesley Estelle Dossey, Escondido, CA (US)

(73) Assignee: Veridex, LLC, Raritan, NJ (US)

( * ) Notice: Subject to any disclaimer, the term of this patent is extended or adjusted under 35 U.S.C. 154(b) by 100 days.

(21) Appl. No.: 12/261,825

(22) Filed: Oct. 30, 2008

(65) Prior Publication Data
US 2009/0136949 A1    May 28, 2009

Related U.S. Application Data

(60) Provisional application No. 60/983,756, filed on Oct. 30, 2007.

(51) Int. Cl.
*C12Q 1/68* (2006.01)
(52) U.S. Cl. ............................................. 435/6
(58) Field of Classification Search ........................ 435/6
See application file for complete search history.

(56) References Cited

U.S. PATENT DOCUMENTS

2007/0299030 A1*  12/2007  Dmitrovsky et al. ............ 514/44
2008/0076674 A1*  3/2008   Litman et al. .................... 506/9

FOREIGN PATENT DOCUMENTS

| JP | 2005 192484 A | 7/2005 |
| WO | WO 2005/111211 A | 11/2005 |
| WO | WO 2007/081720 A | 7/2007 |
| WO | WO 2007/081740 A | 7/2007 |
| WO | WO2009/049129 A1 * | 4/2009 |

OTHER PUBLICATIONS

Weimer et al., The role of microRNAs in cancer: No small matter, European Journal of Cancer, 2007, pp. 1529-1544, vol. 43, Elsevier Ltd.
Garzon et al., MicroRNA expression and function in cancer, Trends in Molecular Medicine, 2006, pp. 580-587, vol. 12, No. 12, Elsevier Ltd.
Nasser et al., Down-regulation of Micro-RNA-1 (miR-1) in Lung Cancer, The Journal of Biological Chemistry, Nov. 28, 2008, pp. 33394-33405, vol. 283, No. 48, The American Society for Biochemistry and Molecular Biology, Inc., USA.
Tusher et al., Significance Analysis of Microarrays Applied to the Ionizing Radiation Response, PNAS, Apr. 24, 2001, pp. 5116-5121, vol. 98, No. 9, National Academy of Sciences.
Perry et al., Rapid Changes in MicroRNA-146a Expression Negatively Regulate the IL-1-β-Induced Inflammatory Response in Human Lung Alveolar Epithelial Cells, The Journal of Immunology, 2008, pp. 5689-5698, vol. 180, The American Association of Immunologists, Inc.
Yan et al., MicroRNA miR-21 overexpression in human breast cancer is associated with advanced clinical stage, lymph node metastasis and patient poor prognosis, RNA Journal, Sep. 23, 2008, pp. 2347-2360, vol. 14, Cold Spring Harbor Laboratory Press.
Dillhoff et al., MicroRNA-21 is Overexpressed in Pancreatic Cancer and a Potential Predictor of Survival, J Gastrointest Surg, 2008, pp. 2171-2176, vol. 12, The Society for Surgery of the Alimentary Tract.
Hayashita et al., A Polycistronic MicroRNA Cluster, miR-17-92, Is Overexpressed in Human Lung Cancers and Enhances Cell Proliferation, Cancer Res 2005, Nov. 1, 2005, pp. 9628-9632, vol. 65 (21), American Association for Cancer Research.
Taganov et al., Nf-kB-dependent induction of microRNA miR-146, and inhibitor targeted to signaling proteins of innate immune responses, PNAS, Aug. 15, 2006, pp. 12481-12486, vol. 103, No. 33, National Academy of Sciences of the USA.
Peltier et al., Normalization of microRNA expression levels in quantitave RT-PCR assays: Identification of suitable reference RNA targets in normal and cancerous human solid tissues, RNA Journal, 2008, pp. 844-852, vol. 14, Cold Spring Harbor Laboratory Press.
Nikiforova et al., MicroRNA Expression Profiling of Thyroid Tumors: Biological Significance and Diagnostic Utility, J Clin Endocrinol Metab., May 2008, pp. 1600-1608, vol. 93 (5), The Endocrine Society.
Chen et al., MicroRNA analysis as a potential diagnostic tool for papillary thyroid carcinoma, Modern Pathology, 2008, pp. 1139-1146, vol. 21, USCAP, Inc.
Connolly et al., Elevated Expression of the miR-17-92 Polycistron and miR-21 in Hepadnavirus-Associated Hepatocellular Carcinoma Contributes to the Malignant Phenotype, The American Journal of Pathology, Sep. 3, 2008, pp. 856-864, vol. 173, No. 3, The American Society for Investigative Pathology.
Calin et al., A MicroRNA Signature Associated with Prognosis and Progression in Chronic Lymphocytic Leukemia, The New England Journal of Medicine, Oct. 27, 2005, pp. 1793-1801, vol. 353, No. 17, The New England Journal of Medicine, Boston.
International Searching Authority, International Search Report and Written Opinion in PCT No. PCT/US2008/081809, Mailed Apr. 1, 2009.
Jay et al., miRNA profiling for diagnosis and prognosis of human cancer, DNA and Cell Biology, May 5, 2007, pp. 1044-5498, vol. 26, No. 5, Mary Ann Liebert, Inc.
Yanaihara et al., Unique microRNA molecular profiles in lung cancer diagnosis and prognosis, Cancer Cell, Mar. 2006, pp. 189-198, vol. 9, No. 3, Elsevier Inc.

* cited by examiner

*Primary Examiner* — Brian Whiteman
(74) *Attorney, Agent, or Firm* — Todd Volyn

(57) ABSTRACT

Disclosed in this specification is a method for predicting the prognosis of squamous cell lung cancer by observing regulatory changes in select miRNA sequences. These sequences may include hsa-mir-146b, hsa-mir-191, hsa-mir-206, hsa-mir-299-3p, hsa-mir-155, hsa-mir-15a, hsa-mir-122a, hsa-mir-513, hsa-mir-184, hsa-mir-511, hsa-mir-100, hsa-mir-10a, hsa-mir-453, hsa-mir-379, hsa-mir-202, hsa-mir-21, hsa-mir-126, hsa-mir-494, hsa-mir-432, hsa-mir-370, and combinations of these sequences.

3 Claims, 1 Drawing Sheet

FIGURE 1A
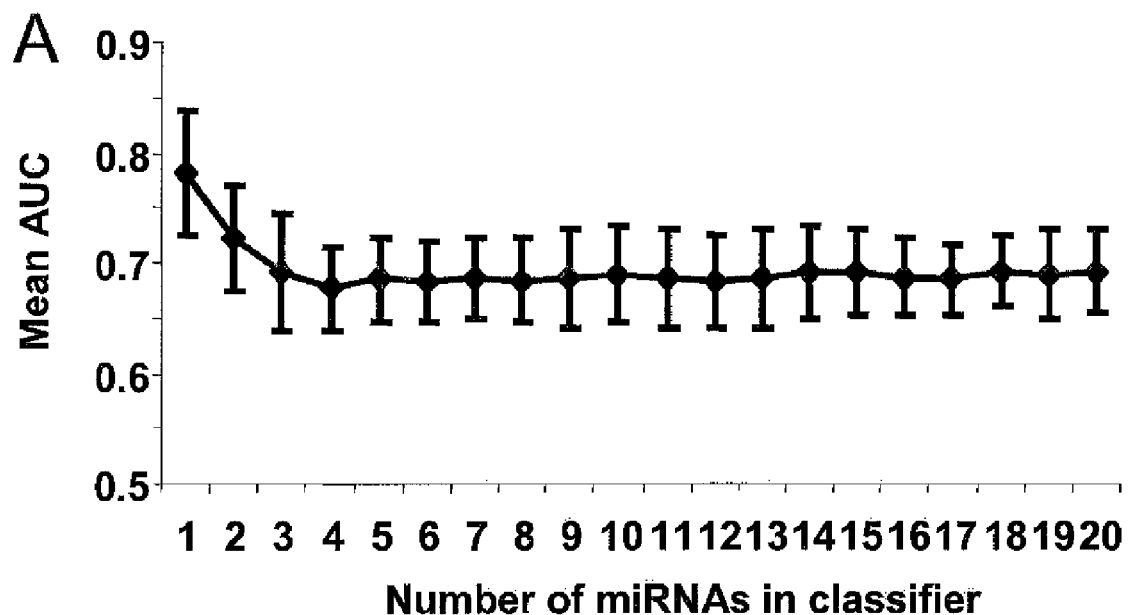
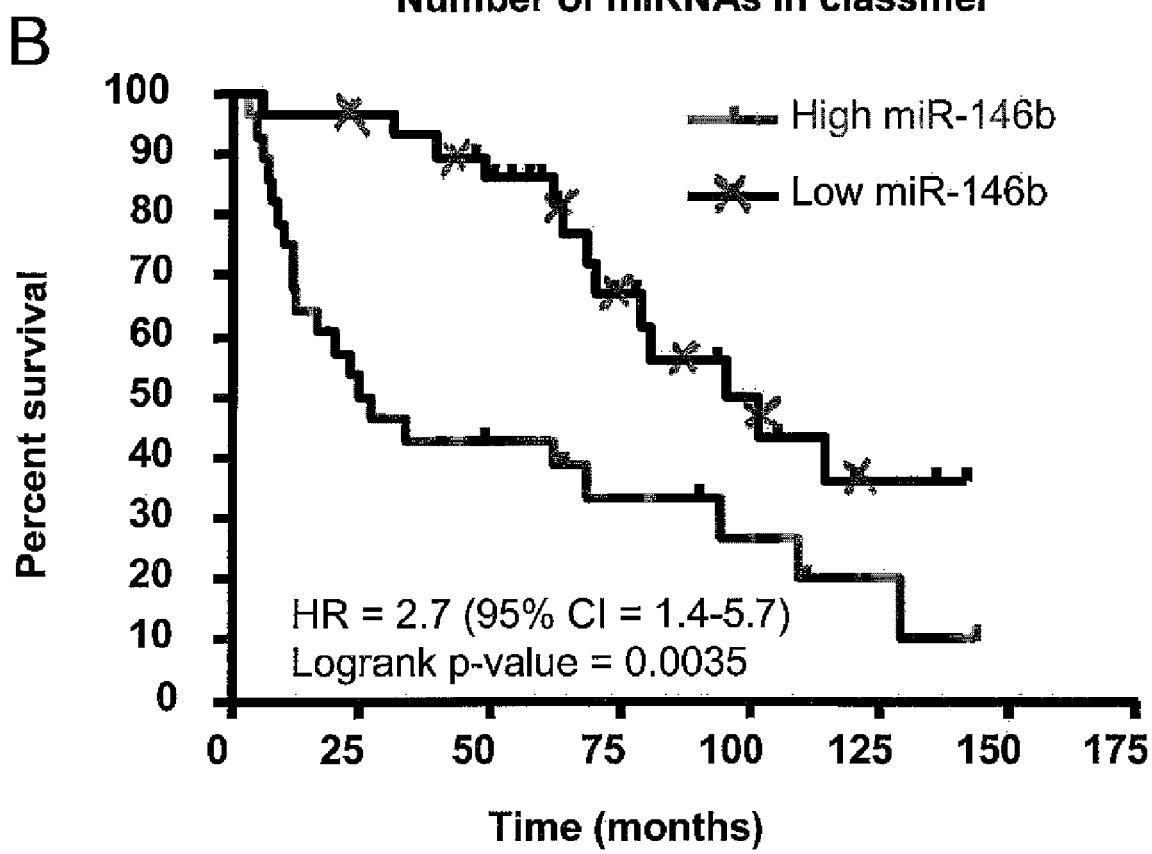
FIGURE 1B

PROCESS FOR PREDICTING THE PROGNOSIS OF SQUAMOUS CELL LUNG CANCER

CROSS-REFERENCE TO RELATED APPLICATIONS

This application claims priority to and the benefit of U.S. provisional patent application Ser. No. 60/983,756, filed Oct. 30, 2007, which application is incorporated herein by reference in its entirety.

REFERENCE TO A SEQUENCE LISTING, A TABLE, OR A PROGRAM LISTING

This application refers to a "Sequence Listing" listed below, which is provided as an electronic document entitled "Sequence listing.txt" (6 kb, created on Oct. 29, 2008), which is incorporated herein by reference in its entirety.

FIELD OF THE INVENTION

This invention relates, in one embodiment, to a method for providing a prognosis of squamous cell lung cancer by observing regulatory changes in the production of select microRNA (miRNA) sequences. By observing up regulation or down regulation of specified sequences, both the presence of cancer cells as well as the prognosis of cancer may be determined.

BACKGROUND OF THE INVENTION

Lung cancer is the most common cause of cancer related deaths worldwide while non-small-cell lung cancers (NSCLC) represent the most frequent type of broncogenic carcinomas. NSCLC is the cause of 80% of all lung cancer deaths in the United States and is composed primarily of, adenocarcinoma, and squamous cell carcinoma (SSC), and to a lesser extent large-cell cancer. Despite potentially curative surgery approximately 40% of patients will relapse within 5 years. Genomic profiling of NSCLC has recently provided insight into predicting the prognosis of patients with this disease. These genomic classifiers can contain up to several hundred genes for the identification of patients with early stage NSCLC who might benefit from chemotherapy in addition to surgical resection.

SUMMARY OF THE INVENTION

The invention comprises, in one form thereof, a method for detecting the presence of squamous cell lung cancer in a cell sample. Applicants have discovered certain miRNAs that are differentially regulated in squamous cell lung cancers relative to wild type cells. By determining the degree of regulatory changes in such miRNAs, one can determine if a tissue sample includes squamous cell lung cancer cells.

In another form the invention is a method for predicting the prognosis of squamous cell lung cancer. Applicants have discovered certain other miRNAs that enable the prognosis to be predicted for a patient with squamous cell lung cancer. By monitoring these miRNAs, a more accurate prognosis may be provided.

BRIEF DESCRIPTION OF THE DRAWINGS

The present invention is disclosed with reference to the accompanying drawings, wherein:

FIG. 1A is a graph that correlates the number of miRNA sequences of interest to predictive prognosis;

FIG. 1B is graph that correlates survival percentage to time for two differing level of miR-146b expression.

Corresponding reference characters indicate corresponding parts throughout the several views. The examples set out herein illustrate several embodiments of the invention but should not be construed as limiting the scope of the invention in any manner.

DETAILED DESCRIPTION

Definitions

The phrase "regulation change" refers to a change in the abundance of a cellular component, such a miRNA, relative to the abundance of the same cellular component in a wild type cell. The phrase "down regulation" refers to a decrease in the abundance of the cellular component in question while the phrase "up regulation" refers to an increase in the abundance of the component.

Identification of Squamous Cell Lung Cancer by Differential miRNA Regulation

Squamous cell lung cancer tissue was compared to wild type tissue and fifteen differentially expressed miRNAs were identified (Table 1). Tissue samples included both cell lines and clinical samples. Total RNA was extracted from the cell samples in accordance with conventional techniques. For example, mirVana isolation kit (Ambion) for snap-frozen samples and the RecoverAll™ Total Nucleic Acid Isolation Kit for formalin-fixed, paraffin-embedded (FFPE) samples (Ambion) may be used. Other conventional RNA extraction methods may also be used. Once the total RNA is extracted, small (less than forty nucleotides) RNA may be isolated by gel electrophoresis. The samples were analyzed to determine the identity and abundance of specific miRNA sequences. Any suitable technique may be used to determine the identity and abundance such as, but not limited to commercially available miRNA kits, such as mirVana Bioarray (Ambion). Fifteen differentially expressed miRNAs were identified in squamous cell lung cancer cells which had significantly altered expression relative to a wild type sample. These sequences are shown in Table 1.

TABLE 1 miRNAs differentially expressed between normal lung and lung squamous cell carcinoma.

| SEQ ID | Name | Fold Change | mean LN | mean LC | Dir |
| --- | --- | --- | --- | --- | --- |
| SEQ ID NO. 1 | hsa-mir-210 | 3.25 | 6.0 | 7.7 | up |
| SEQ ID NO. 2 | hsa-mir-200c | 2.46 | 9.5 | 10.8 | up |
| SEQ ID NO. 3 | hsa-mir-17-5p | 2.14 | 6.4 | 7.5 | up |
| SEQ ID NO. 4 | hsa-mir-20a | 1.41 | 5.6 | 6.1 | up |
| SEQ ID NO. 5 | hsa-mir-125a | 0.41 | 10.20 | 8.9 | down |
| SEQ ID NO. 6 | hsa-let-7e | 0.76 | 9.5 | 9.1 | down |
| SEQ ID NO. 7 | hsa-mir-200a | 2.46 | 5.7 | 7.0 | up |
| SEQ ID NO. 8 | hsa-mir-106b | 2.00 | 5.9 | 6.9 | up |
| SEQ ID NO. 9 | hsa-mir-93 | 2.46 | 7.5 | 8.8 | up |
| SEQ ID NO. 10 | hsa-mir-182 | 2.30 | 5.6 | 6.8 | up |
| SEQ ID NO. 11 | hsa-mir-183 | 1.62 | 5.6 | 6.3 | up |
| SEQ ID NO. 12 | hsa-mir-106a | 2.30 | 6.5 | 7.7 | up |
| SEQ ID NO. 13 | hsa-mir-20b | 1.87 | 5.2 | 6.1 | up |
| SEQ ID NO. 14 | hsa-mir-224 | 2.64 | 5.5 | 6.9 | up |

LN = lung normal signal intensity (log2);
LC = lung cancer signal intensity (log2)
Fold Change = $2^{(LC-LN)}$ In one embodiment of the invention, a sample is analyzed to determine the abundance of a specified miRNA sequence from Table 1. The sample may be a tissue sample, such as a sample obtained during a surgical procedure. Alternatively, the sample may be obtained non-invasively from, for example, a blood sample or from a similar source. The abundance of a specified miRNA in the sample is determined and a regulation change is observed relative to an average sample. Since miRNAs are known to persist outside of the cell, free miRNAs can provide a screening method for squamous cell lung cancer. Such screening can be performed using non-invasive sampling techniques, such as a simple blood test. In this fashion patients in a high-risk group could be routinely tested to help identify the early development of cancer.

In another embodiment, miRNA abundances are observed to distinguish squamous cell lung cancer from adenocarcinoma. By observing regulatory changes in miRNA expression, such a distinction can be made even when tissue morphology is unclear.

Prognosis of Lung Squamous Cell Carcinoma

Additional miRNA sequences have been discovered that permit one to predict the prognosis of lung squamous cell carcinoma. Twenty miRNA sequences were so identified as being tightly associated with squamous cell lung carcinoma prognosis. Clinical samples were collected between October 1991 and July 2002. The medical history of each of the patents was also collected and a correlation was made between those miRNAs that expressed altered regulations and the patients prognosis. The details of this correlation process are discussed elsewhere in this specification. In this manner, those miRNA sequences which strongly influence patient prognosis were identified. The identified sequences are listed in Table 2.

TABLE 2 miRNAs associated with squamous cell lung carcinoma prognosis.

| SEQ ID | Name | Fold Change | mean_0 | mean_1 | Dir |
|---|---|---|---|---|---|
| SEQ ID NO. 15 | hsa-mir-146b | 1.51 | 6.97 | 7.57 | up |
| SEQ ID NO. 16 | hsa-mir-191 | 1.23 | 8.53 | 8.83 | up |
| SEQ ID NO. 17 | hsa-mir-206 | 0.82 | 6.13 | 5.84 | down |
| SEQ ID NO. 18 | hsa-mir-299-3p | 0.82 | 6.19 | 5.90 | down |
| SEQ ID NO. 19 | hsa-mir-155 | 1.33 | 7.17 | 7.58 | up |
| SEQ ID NO. 20 | hsa-mir-15a | 1.21 | 6.24 | 6.51 | up |
| SEQ ID NO. 21 | hsa-mir-122a | 0.74 | 6.86 | 6.42 | down |
| SEQ ID NO. 22 | hsa-mir-513 | 0.8 | 6.99 | 6.67 | down |
| SEQ ID NO. 23 | hsa-mir-184 | 0.71 | 6.72 | 6.24 | down |
| SEQ ID NO. 24 | hsa-mir-511 | 1.23 | 6.56 | 6.85 | up |
| SEQ ID NO. 25 | hsa-mir-100 | 1.27 | 7.15 | 7.50 | up |
| SEQ ID NO. 26 | hsa-mir-10a | 1.24 | 6.45 | 6.77 | up |
| SEQ ID NO. 27 | hsa-mir-453 | 0.74 | 7.18 | 6.75 | down |
| SEQ ID NO. 28 | hsa-mir-379 | 0.78 | 6.68 | 6.32 | down |
| SEQ ID NO. 29 | hsa-mir-202 | 0.62 | 7.89 | 7.20 | down |
| SEQ ID NO. 30 | hsa-mir-21 | 1.41 | 9.32 | 9.81 | up |
| SEQ ID NO. 31 | hsa-mir-126 | 1.27 | 7.60 | 7.94 | up |
| SEQ ID NO. 32 | hsa-mir-494 | 0.63 | 10.53 | 9.87 | down |
| SEQ ID NO. 33 | hsa-mir-432 | 0.67 | 7.97 | 7.40 | down |
| SEQ ID NO. 34 | hsa-mir-370 | 0.79 | 7.25 | 6.90 | down |

Mean_0 and Mean_1 are wild type and cancerous tissues, respectively.

Using a five-fold cross validation, it was found that the highest mean value for predicting overall survival within three years was 78% when using miR-146b alone (SEQ ID NO. 15). When three or more additional miRNAs were added to Mir-146b in a linear fashion, the predictive accuracy dropped by approximately 68%, but thereafter stabilized. See FIG. 1A. Patients with high miR-146 up regulation had significantly worse overall survival (26 months) compared to the low miRNA-146b group (95 months). See FIG. 1B. In FIG. 1B, a "high" miRNA-146 group (the lower of the two lines) was defined as those with miRNA-146 levels above the median value. The "low" miRNA-146 group (the higher of the two lines) was defined as those with miRNA-146 below the median value.

By measuring the abundance of specified miRNA sequences a predicted prognosis may be provided to a patient. For example, statistical data may be gathered that correlates miRNA abundance of a specific sequence to patent survivability as a function of time. For example, for a patient with a large regulatory change in a certain miRNA sequence, the data may indicate that remission is 78% likely within the next three years. This predicted prognosis may be provided to the patient. FIG. 1B provides sample data for miR-146b, but such data should not be construed as limiting. Additional data, such as the demographic information of the patient, may be taken into consideration such broader statistical information is gathered.

The miRNA may be extracted from a tissue sample using conventional techniques. Such a sample may be obtained during a surgical procedure. Alternatively, miRNA may be isolated from a non-tissue sample. For example, miRNA may be isolated from a blood, stool, urine or other biological sample. The abundance of the specific miRNA found in the sample is compared to a normal sample. Up regulated or down regulated miRNA abundances may be indicative of a cancer.

The abundance of the specified miRNA sequence(s) may be determined in accordance with any known technique. By way of illustration, but not limitation, QPCR may be used.

The miRNA sequences in the attached sequence listing represent commonly isolated miRNA sequences. Alterations at the termini of the listed sequences are known in the art and fall within the scope of the invention provided that the residues are at least 95% homologous.

While the invention has been described with reference to specific embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed or the particular mode contemplated for carrying out this invention, but that the invention will include all embodiments falling within the scope and spirit of the appended claims.

Methods

Clinical Samples

In total, sixty-one snap-frozen lung SCC and 10 matched normal adjacent lung tissue samples were evaluated for miRNA expression. These samples were collected from patients from the University of Michigan Hospital between October 1991 and July 2002 with patient consent and Institutional Review Board approval. Samples chosen for analysis contained greater than 70% tumor cells. Of the sixty-one tumor samples fifty-seven had sufficient follow up clinical information and were used for prognostic analysis. Fifty-four of the fifty-seven were previously profiled using the Affymetrix U133A GeneChip (GSE4573).

Ambion miRNA Expression Profiling

The mirVana Bioarray (Ambion, version 2) that contains 328 human miRNA probes was employed to identify lung SCC miRNA signatures. Total RNA was isolated using Trizol. MiRNA was isolated from 4 ug of total RNA using the mirVana isolation kit (Ambion). All samples were then fractionated by polyacrylamide gel electrophoresis (Flash-Page Ambion) and small RNAs (<40 nt) were recovered by ethanol precipitation with linear acrylamide. Quantitative RT-PCR (qPCR) of miR-16 was used to confirm miRNA enrichment prior to miRNA array analysis. If the Ct value of miR-16 was greater than 25 then the miRNA isolation was considered a failure.

The small RNA samples were subject to poly(A) polymerase reaction wherein amine modified uridines were incorporated (Ambion). The tailed samples were then fluorescently labeled using the amine-reactive Cy3 (Invitrogen). The aforementioned labeling technique is only one possible methodology. Other suitable labeling techniques would be apparent to those skilled in the art after benefiting from reading this specification. Such alternative methods are contemplated for use with the instant specification. The fluorescently labeled RNAs were purified using a glass-fiber filter and eluted (Ambion). Each sample was then hybridized to the Bioarray slides for 14 hours at 42° C. (Ambion). The arrays were washed and scanned using an Agilent 2505B confocol laser microarray scanner (Agilent) and data was obtained using the Expression Analysis software (Codelink, version 4.2).

miRNA Quantitative PCR

Quantitative PCR (QPCR) was performed using the ABI miRNA Taqman reagents to verify miRNA expression profiles. Ten ng of total RNA was converted to cDNA using the High Capacity DNA Archive kit and 3 ul of 5×RT primer according to the manufacturer's instructions (Ambion). The 15 µl reactions were incubated in a thermocycler for 30 min at 16° C., 30 min at 42° C., 5 min at 85° C. and held at 4° C. All reverse transcriptase reactions included no template controls. QPCR was performed using a standard Taqman® PCR kit protocol on an Applied Biosystems 7900HT Sequence Detection System. The 10 µl PCR reaction included 0.66 µl RT product, 1 µl Taqman miRNA assay primer and probe mix, 5 µl Taqman 2× Universal PCR master mix (No Amperase UNG) and 3.34 µl water. The reactions were incubated in a 384 well plate at 95° C. for 10 min, followed by 40 cycles of 95° C. for 15 sec, and 60° C. for 2 min. All QPCR reactions included a no cDNA control and all reactions were performed in triplicate.

MiRNA Statistical Analyses

Probes flagged by the Expression Analysis software were first removed and background median values were subtracted from the spot mean. Outlier samples were identified and removed if the number of flagged probes was less than the mean minus the standard deviation of flagged probes per chip. Spot intensity values below zero were set to 0.5 and the data was then quantile normalized. A background cutoff of 6 (log 2 normalized) was identified by plotting the correlations of replicate probes across all samples versus the median of median intensities. Therefore, miRNAs were removed from further analyses if the normalized signal intensity was less than 6 in either comparison group. This cutoff was chosen since the correlation of replicate probes dropped precipitously below this value.

Survival analysis was performed using the Significance of Microarray Analysis (SAM) algorithm (Tusher V G, Tibshirani R, Chu G. Significance analysis of microarrays applied to the ionizing radiation response. Proc Natl Acad Sci USA 2001; 98(9):5116-21). MiRNAs were selected as being significantly associated with overall survival if the paired t-test p-value was less than 0.05 and the area under the curve (AUC) from a receiver operator characteristic analysis was greater than 0.65 using a 3-year cut-off. A maximum 3 years follow-up was employed since the majority of patients who will relapse in this population will do so within 3 years. Also many of these patients were aged and death due to non-cancer related illnesses would likely increase after 3 years. To determine the minimum number of miRNAs used to construct a prognostic classifier, combinations of gene expression markers were tested by adding one gene at a time according to the rank order. For each signature with increasing number of genes, Receiver Operating Characteristic (ROC) analysis using death within 3 years as the defining point was performed, in 100 5-fold cross validations, to calculate the average area under the curve (AUC).

What is claimed is:

1. A process for predicting the prognosis of squamous cell lung cancer in humans comprising the steps of:
   extracting total RNA from a sample of lung tissue;
   observing up regulation change of SEQ ID NO. 15 within extracted RNA relative to the same microRNA in a wild type lung tissue sample; and
   predicting a poorer prognosis of squamous cell lung carcinoma based on the observation than would be the case if no up regulation was observed.

2. A process for predicting the prognosis of squamous cell lung cancer in humans comprising the steps of:
   observing up regulation change of SEQ ID NO. 15 within extracted RNA relative to the same microRNA in a wild type lung tissue sample; wherein the step of observing includes the step of performing a quantitative polymerase chain reaction; and
   predicting a poorer prognosis of squamous cell lung carcinoma based on the observation than would be the case if no up regulation was observed.

3. A process for predicting the prognosis of squamous cell lung cancer in humans comprising the steps of:
   observing the abundance of SEQ ID NO. 15 within a sample, wherein the step of observing includes the step of performing a quantitative polymerase chain reaction; and
   predicting a prognosis of squamous cell lung carcinoma based on the observation.

* * * * *

SEQUENCE LISTING

```
<160> NUMBER OF SEQ ID NOS: 34

<210> SEQ ID NO 1
<211> LENGTH: 22
<212> TYPE: RNA
<213> ORGANISM: Homo sapiens

<400> SEQUENCE: 1
cugugcgugu gacagcggcu ga                                             22

<210> SEQ ID NO 2
<211> LENGTH: 22
<212> TYPE: RNA
<213> ORGANISM: Homo sapiens

<400> SEQUENCE: 2
uaauacugcc ggguaaugau gg                                             22

<210> SEQ ID NO 3
<211> LENGTH: 24
<212> TYPE: RNA
<213> ORGANISM: Homo sapiens

<400> SEQUENCE: 3
```

-continued

| | |
|---|---|
| caaagugcuu acagugcagg uagu | 24 |

<210> SEQ ID NO 4
<211> LENGTH: 23
<212> TYPE: RNA
<213> ORGANISM: Homo sapiens

<400> SEQUENCE: 4

| | |
|---|---|
| uaaagugcuu auagugcagg uag | 23 |

<210> SEQ ID NO 5
<211> LENGTH: 23
<212> TYPE: RNA
<213> ORGANISM: Homo sapiens

<400> SEQUENCE: 5

| | |
|---|---|
| ucccugagac ccuuuaaccu gug | 23 |

<210> SEQ ID NO 6
<211> LENGTH: 21
<212> TYPE: RNA
<213> ORGANISM: Homo sapiens

<400> SEQUENCE: 6

| | |
|---|---|
| ugagguagga gguuguauag u | 21 |

<210> SEQ ID NO 7
<211> LENGTH: 22
<212> TYPE: RNA
<213> ORGANISM: Homo sapiens

<400> SEQUENCE: 7

| | |
|---|---|
| uaacacuguc ugguaacgau gu | 22 |

<210> SEQ ID NO 8
<211> LENGTH: 21
<212> TYPE: RNA
<213> ORGANISM: Homo sapiens

<400> SEQUENCE: 8

| | |
|---|---|
| uaaagugcug acagugcaga u | 21 |

<210> SEQ ID NO 9
<211> LENGTH: 22
<212> TYPE: RNA
<213> ORGANISM: Homo sapiens

<400> SEQUENCE: 9

| | |
|---|---|
| aaagugcugu ucgugcaggu ag | 22 |

<210> SEQ ID NO 10
<211> LENGTH: 22
<212> TYPE: RNA
<213> ORGANISM: Homo sapiens

<400> SEQUENCE: 10

| | |
|---|---|
| uuuggcaaug guagaacuca ca | 22 |

<210> SEQ ID NO 11
<211> LENGTH: 22
<212> TYPE: RNA
<213> ORGANISM: Homo sapiens

<400> SEQUENCE: 11

| | |
|---|---|
| uauggcacug guagaauuca cu | 22 |

<210> SEQ ID NO 12
<211> LENGTH: 23
<212> TYPE: RNA
<213> ORGANISM: Homo sapiens

<400> SEQUENCE: 12

| | |
|---|---|
| aaaagugcuu acagugcagg uag | 23 |

<210> SEQ ID NO 13
<211> LENGTH: 23
<212> TYPE: RNA
<213> ORGANISM: Homo sapiens

<400> SEQUENCE: 13

| | |
|---|---|
| caaagugcuc auagugcagg uag | 23 |

<210> SEQ ID NO 14
<211> LENGTH: 23
<212> TYPE: RNA
<213> ORGANISM: Homo sapiens

<400> SEQUENCE: 14

| | |
|---|---|
| caagucacua gugguuccgu uua | 23 |

<210> SEQ ID NO 15
<211> LENGTH: 22
<212> TYPE: RNA
<213> ORGANISM: Homo sapiens

<400> SEQUENCE: 15

| | |
|---|---|
| ugagaacuga auuccauagg cu | 22 |

<210> SEQ ID NO 16
<211> LENGTH: 22
<212> TYPE: RNA
<213> ORGANISM: Homo sapiens

<400> SEQUENCE: 16

| | |
|---|---|
| caacggaauc ccaaaagcag cu | 22 |

<210> SEQ ID NO 17
<211> LENGTH: 22
<212> TYPE: RNA
<213> ORGANISM: Homo sapiens

<400> SEQUENCE: 17

| | |
|---|---|
| uggaauguaa ggaagugugu gg | 22 |

<210> SEQ ID NO 18
<211> LENGTH: 22
<212> TYPE: RNA
<213> ORGANISM: Homo sapiens

<400> SEQUENCE: 18

| | |
|---|---|
| uauguggau gguaaaccgc uu | 22 |

<210> SEQ ID NO 19
<211> LENGTH: 22
<212> TYPE: RNA
<213> ORGANISM: Homo sapiens

<400> SEQUENCE: 19

```
uuaaugcuaa ucgugauagg gg                                              22

<210> SEQ ID NO 20
<211> LENGTH: 22
<212> TYPE: RNA
<213> ORGANISM: Homo sapiens

<400> SEQUENCE: 20
uagcagcaca uaaugguuug ug                                              22

<210> SEQ ID NO 21
<211> LENGTH: 23
<212> TYPE: RNA
<213> ORGANISM: Homo sapiens

<400> SEQUENCE: 21
uggaguguga caauggguguu ugu                                            23

<210> SEQ ID NO 22
<211> LENGTH: 22
<212> TYPE: RNA
<213> ORGANISM: Homo sapiens

<400> SEQUENCE: 22
uucacaggga ggugucauuu au                                              22

<210> SEQ ID NO 23
<211> LENGTH: 22
<212> TYPE: RNA
<213> ORGANISM: Homo sapiens

<400> SEQUENCE: 23
uggacggaga acugauaagg gu                                              22

<210> SEQ ID NO 24
<211> LENGTH: 21
<212> TYPE: RNA
<213> ORGANISM: Homo sapiens

<400> SEQUENCE: 24
gugucuuuug cucugcaguc a                                               21

<210> SEQ ID NO 25
<211> LENGTH: 22
<212> TYPE: RNA
<213> ORGANISM: Homo sapiens

<400> SEQUENCE: 25
aacccguaga uccgaacuug ug                                              22

<210> SEQ ID NO 26
<211> LENGTH: 23
<212> TYPE: RNA
<213> ORGANISM: Homo sapiens

<400> SEQUENCE: 26
uacccuguag auccgaauuu gug                                             23

<210> SEQ ID NO 27
<211> LENGTH: 22
<212> TYPE: RNA
<213> ORGANISM: Homo sapiens

<400> SEQUENCE: 27
```

```
gagguugucc guggugaguu cg                                                        22

<210> SEQ ID NO 28
<211> LENGTH: 19
<212> TYPE: RNA
<213> ORGANISM: Homo sapiens

<400> SEQUENCE: 28
ugguagacua uggaacgua                                                            19

<210> SEQ ID NO 29
<211> LENGTH: 22
<212> TYPE: RNA
<213> ORGANISM: Homo sapiens

<400> SEQUENCE: 29
agagguauag ggcaugggaa aa                                                        22

<210> SEQ ID NO 30
<211> LENGTH: 22
<212> TYPE: RNA
<213> ORGANISM: Homo sapiens

<400> SEQUENCE: 30
uagcuuauca gacugauguu ga                                                        22

<210> SEQ ID NO 31
<211> LENGTH: 21
<212> TYPE: RNA
<213> ORGANISM: Homo sapiens

<400> SEQUENCE: 31
ucguaccgug aguaauaaug c                                                         21

<210> SEQ ID NO 32
<211> LENGTH: 22
<212> TYPE: RNA
<213> ORGANISM: Homo sapiens

<400> SEQUENCE: 32
ugaaacauac acgggaaacc uc                                                        22

<210> SEQ ID NO 33
<211> LENGTH: 23
<212> TYPE: RNA
<213> ORGANISM: Homo sapiens

<400> SEQUENCE: 33
ucuuggagua ggucauuggg ugg                                                       23

<210> SEQ ID NO 34
<211> LENGTH: 21
<212> TYPE: RNA
<213> ORGANISM: Homo sapiens

<400> SEQUENCE: 34
gccugcuggg guggaaccug g                                                         21
```